United States Patent
Sutton et al.

(10) Patent No.: US 9,216,144 B2
(45) Date of Patent: *Dec. 22, 2015

(54) HAIR TREATMENT PROCESS PROVIDING DISPERSED COLORS BY LIGHT DIFFRACTION

(71) Applicants: The Procter & Gamble Company, Cincinnati, OH (US); Los Alamos National Security LLC, Los Alamos, NM (US)

(72) Inventors: Richard Matthew Charles Sutton, Cincinnati, OH (US); Bruce Carvell Lamartine, Los Alamos, NM (US); E. Bruce Orler, Blacksburg, VA (US); Shuangqi Song, Houston, TX (US)

(73) Assignees: The Procter & Gamble Company, Cincinnati, OH (US); Los Alamos National Security LLC, Los Alamos, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/229,414

(22) Filed: Mar. 28, 2014

(65) Prior Publication Data

US 2014/0290689 A1 Oct. 2, 2014

Related U.S. Application Data

(60) Provisional application No. 61/806,044, filed on Mar. 28, 2013.

(51) Int. Cl.
*A61K 8/18* (2006.01)
*A61Q 5/00* (2006.01)

(Continued)

(52) U.S. Cl.
CPC ............. *A61K 8/18* (2013.01); *A61K 8/8129* (2013.01); *A61K 8/8152* (2013.01); *A61K 8/85* (2013.01); *A61K 8/87* (2013.01); *A61Q 5/065* (2013.01); *A45D 19/00* (2013.01); *A45D 2019/0091* (2013.01)

(58) Field of Classification Search
CPC ...... A45D 19/02; A45D 19/0025; A61Q 5/04; A61Q 5/06; A61Q 5/02; A61Q 5/12; A61K 8/46

See application file for complete search history.

(56) References Cited

U.S. PATENT DOCUMENTS 6,583,933 B2 6/2003 Lamartine
6,822,030 B2 11/2004 Olson (Continued)

FOREIGN PATENT DOCUMENTS

EP 0524346 B1 6/1998
JP 2010030920 A1 2/2010
WO WO2011160098 A2 12/2011

*Primary Examiner* — Robyn Doan
(74) *Attorney, Agent, or Firm* — James T. Fondriest

(57) ABSTRACT

A hair treatment process for providing dispersed colors by light diffraction including (a) coating the hair with a material comprising a polymer, (b) pressing the hair with a pressing device including one or more surfaces, and (c) forming a secondary nanostructured surface pattern on the hair that is complementary to the primary nanostructured surface pattern on the one or more surfaces of the pressing device. The secondary nanostructured surface pattern diffracts light into dispersed colors that are visible on the hair. The section of the hair is pressed with the pressing device for from about 1 to 55 seconds. The polymer has a glass transition temperature from about 55° C. to about 90° C. The one or more surfaces include a primary nanostructured surface pattern.

20 Claims, 8 Drawing Sheets

(51) Int. Cl.
*A61Q 5/06* (2006.01)
*A61K 8/81* (2006.01)
*A61K 8/85* (2006.01)
*A61K 8/87* (2006.01)
*A45D 19/00* (2006.01)

(56) References Cited

U.S. PATENT DOCUMENTS

| | | | |
|---|---|---|---|
| 6,855,371 | B2 | 2/2005 | Gler |
| 7,083,805 | B2 | 8/2006 | Begleiter |
| 7,625,513 | B2 | 12/2009 | Yu |
| 8,607,803 | B2 * | 12/2013 | Lamartine et al. ............ 132/208 |
| 8,881,743 | B2 * | 11/2014 | Lamartine et al. ............ 132/208 |
| 2002/0159965 | A1 | 10/2002 | Frechet |
| 2007/0141002 | A1 | 6/2007 | Montezinos |
| 2008/0019925 | A1 | 1/2008 | Begleiter |
| 2008/0312395 | A1 | 12/2008 | Muller |
| 2009/0186055 | A1 | 7/2009 | Dumousseaux |
| 2009/0264836 | A1 | 10/2009 | Roe |
| 2010/0086801 | A1 | 4/2010 | Russell |
| 2010/0120116 | A1 | 5/2010 | Kaplan |
| 2010/0135918 | A1 | 6/2010 | Kim |
| 2010/0139681 | A1 | 6/2010 | Oshika |
| 2010/0263683 | A1 | 10/2010 | Dutheil-Gouret |
| 2010/0307553 | A1 | 12/2010 | Defries |
| 2011/0135697 | A1 | 6/2011 | Omenetto |
| 2013/0000661 | A1 | 1/2013 | Fondin |
| 2013/0052419 | A1 | 2/2013 | Yializis |
| 2014/0069454 | A1 | 3/2014 | Lamartine |
| 2014/0076347 | A1 | 3/2014 | Lamartine |

* cited by examiner

Motheye structure:
Rectangular pits with different pitch in vertical and horizontal directions ID COLORS BY LIGHT
HAIR TREATMENT PROCESS PROVIDING DISPERSED COLORS BY LIGHT DIFFRACTION

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

Provided is a process for providing dispersed colors by light diffraction comprising coating the hair with a polymer and pressing the hair with one or more surfaces comprising a nanostructured surface pattern.

BACKGROUND OF THE INVENTION

Almost all hair coloring methods use colorants (dyes, for example) that change the color of the hair and produce a single color from the treated hair. Coloring methods include methods for permanent coloring and methods for temporary coloring.

Permanent coloring methods typically use ammonia to open up a hair cuticle so that colorants may be deposited on the underlying hair cortex. Peroxide is used to drive formation of new color and to remove existing natural and artificial pigments.

Temporary methods also use colorants such as acidic dyes that do not significantly penetrate the cuticle. Temporary methods also don't use ammonia. Shampooing eventually washes out temporary colorants and the hair's natural pigment is retained. Ground silica suspended in a polymer has also been used to create a temporary iridescent effect.

Fiber coloration with little or no colorants occurs in nature. Peacock feathers, for example, are known to have little or no pigmentation. The striking colors in peacock feathers are produced primarily from diffraction of incident light from nanometer scale branches of the peacock feathers. Such an effect is desired for human hair.

Based on the forgoing, there is a need for a hair treatment process for providing dispersed colors by light diffraction on human hair.

SUMMARY OF THE INVENTION

According to an embodiment of the invention, there is provided a hair treatment process for providing dispersed colors by light diffraction comprising (a) coating the hair with a material comprising a polymer, wherein the polymer has a glass transition temperature from about 55° C. to about 90° C.; (b) pressing the hair with a pressing device comprising one or more surfaces, wherein the one or more surfaces each comprise a primary nanostructured surface pattern; and (c) forming a secondary nanostructured surface pattern on the hair that is complementary to the primary nanostructured surface pattern on the one or more surfaces of the pressing device; wherein the secondary nanostructured surface pattern diffracts light into dispersed colors that are visible on the hair; and wherein the section of the hair is pressed with the pressing device for from about 1 to 55 seconds.

According to another embodiment of the invention, there is provided a hair treatment process for providing dispersed colors by light diffraction comprising (a) coating the hair with a material comprising a polymer, wherein the polymer has a glass transition temperature from about 55° C. to about 90° C.; (b) pressing a section of the hair with a pressing device comprising two or more surfaces, wherein the two or more surfaces each comprise a primary nanostructured surface pattern; and (c) forming a secondary nanostructured surface pattern on the section of the hair that is complementary to the primary nanostructured surface patterns on the two or more surfaces of the pressing device; wherein the secondary nanostructured surface pattern diffracts light into dispersed colors that are visible on the section of the hair.

According to yet another embodiment of the invention, there is provided a hair treatment process for providing dispersed colors by light diffraction comprising (a) coating the hair with a material comprising a polymer, wherein the polymer has a glass transition temperature from about 55° C. to about 90° C.; (b) pressing the hair with a pressing device comprising one or more surfaces, wherein the one or more surfaces each comprise a primary nanostructured surface pattern; and (c) forming a secondary nanostructured surface pattern on the hair that is complementary to the primary nanostructured surface pattern on the one or more surfaces of the pressing device; wherein the secondary nanostructured surface pattern diffracts light into dispersed colors that are visible on the hair; and wherein the press does not comprise a heating element.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION OF THE INVENTION

Figure 1:
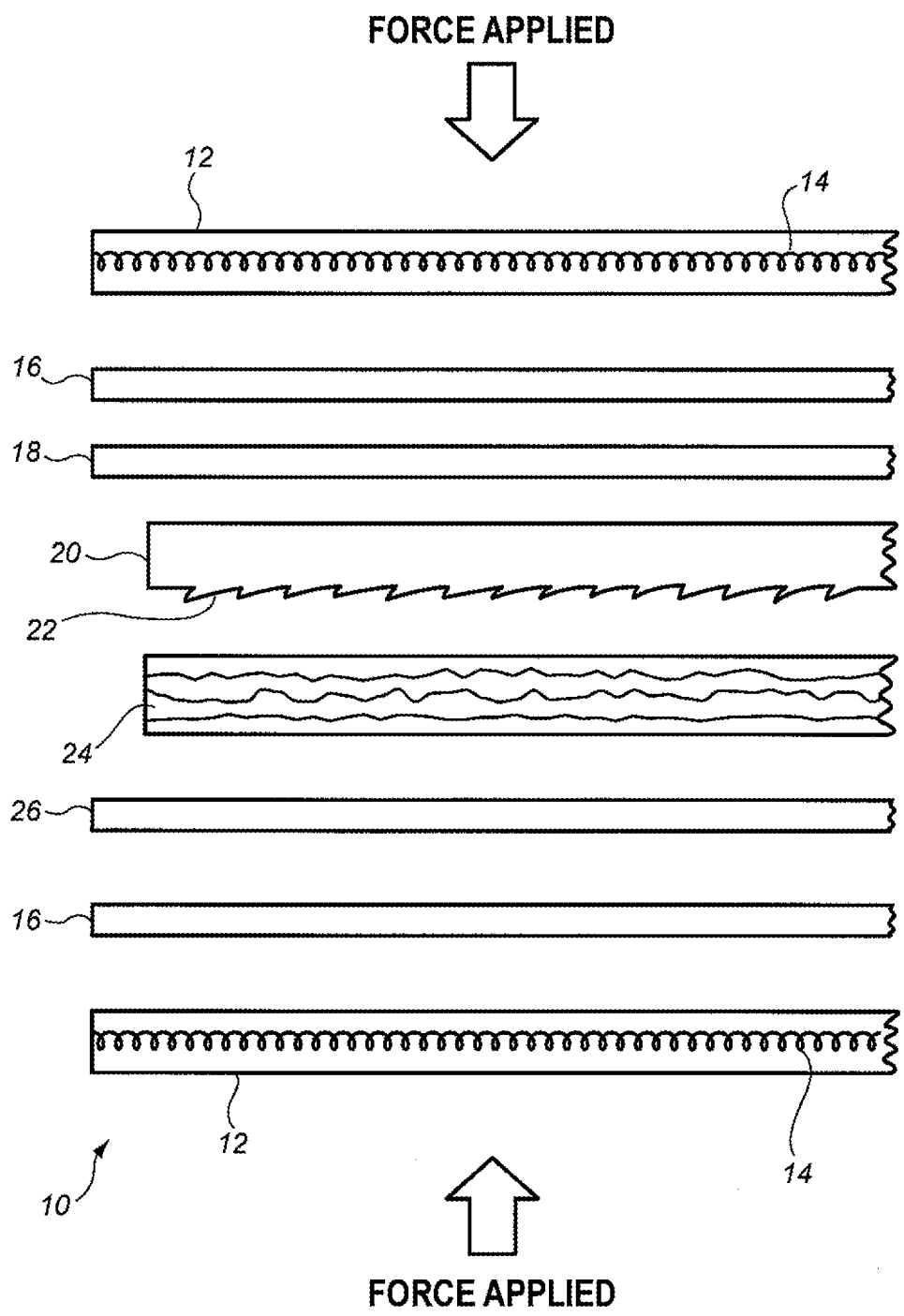
FIG. 1 shows a sketch of hot-pressing a sample of fluid-coated hair according to an embodiment of the invention.

To achieve the foregoing and other objects, and in accordance with the purposes of the present invention, as embodied and broadly described herein, the present invention provides a hair treatment process. The process involves coating hair with a polymer-containing material of a suitable soluble (and/or dispersible) polymer and inserting the coated hair into a pressing device capable of both transforming the material into a film and forming on a surface of the film a nanostructured pattern suitable for producing colors by light diffraction. In an embodiment, the hair is cleaned and dried before coating the hair with the material. The material may optionally include a plasticizer. Optionally, the material includes a surfactant. The material-coated hair may be pressed under conditions suitable for forming a secondary nanostructured surface pattern on the hair that is complementary to the primary nanostructured surface pattern on the one or more surfaces of the pressing device. The hair and film may be cooled and then removed from the pressing device. Exposure of the coated hair to incident polychromatic light (e.g. sunlight, theatrical light) results in dispersed colored light from light diffracted from the film. In an embodiment, the material may be a fluid. In an embodiment, the polymer has a glass transition temperature from about 55° C. to about 90° C. In an embodiment, the hair may be pressed for from about 1 to 55 seconds, alternatively for from about 1 to about 50 seconds, alternatively for from about 1 to about 45 seconds, alternatively for from about 1 to about 40 seconds, alternatively for from about 1 to about 30 seconds, and alternatively for from about 1 to about 15 seconds.

The invention is also concerned with a pressing device for treating hair. In an embodiment, the pressing device may be a heating iron. The pressing device may include all of the elements of a conventional heating iron with the exception of one or more heating blocks that have been configured with a primary nanostructured surface pattern suitable for forming a complementary secondary nanostructured pattern in a flexible film formed when a sample of hair coated with a material including a polymer with a glass transition temperature of from about 55 degrees Celsius to about 90 degrees Celsius is hot pressed using the heating block. In an embodiment, the invention may also be a pressing device as described above without a heating element. In an embodiment, the pressing device may have two surfaces each comprising a nanostructured surface pattern.

Hair treated by the provided method becomes coated with a polymer film that diffracts light to produce dispersed colored light. In an embodiment, a color spectrum results from light diffraction from a secondary nanostructured surface pattern imprinted onto a polymer film coated onto the hair. The nano-pattern is formed by coating the hair with a fluid that includes a polymer and hot pressing the fluid-coated hair under a few pounds per square inch (psi) pressure using a hot press that includes one or more suitably modified heating blocks each comprising a primary nanostructured surface pattern capable of forming a secondary nanostructured surface pattern on the hair. In an embodiment, the method may provide a temporary coloration effect because the polymer may be shampooed out of the hair. In an embodiment, the method may provide a permanent or semi-permanent coloration effect. In an embodiment, the coloration effect may be removed by using heat.

The primary nanostructured surface pattern can be incorporated into one or more surfaces of a handheld device similar to a common hair flatiron. The primary nanostructured surface pattern may be suitably configured to provide a secondary nanostructured surface pattern in film coated hair to produce a rainbow of colors. The primary nanostructured surface pattern may be suitably configured to produce directionally specific images in the polymer coated hair.

In an embodiment, the hair treatment process as described may be used to impart highlighting effects on the hair by treating individual hair strands. In an embodiment, the hair treatment process may be applied to other hair-like materials that may be secured to the hair or scalp as a hair extension or by any other means suitable for giving the desired nanostructured effects.

The net effect of applying the method to hair may be that when the hair changes position relative to a dominant light source, such as sunlight or theatrical lights, the hair color and any images incorporated into the hair change as well.

Different nano-patterned blocks may be used for different multiple color or image effects in the treated hair.

The hair treatment method may form a composite of hair and polymer-containing film and may create a nanostructured pattern in the film that produces dispersed colored light. Non-limiting examples of suitable polymers useful with this invention are soluble and/or dispersible in water or alcohol, do not damage the hair, and have a glass transition temperature (Tg) in a range such that a film can be formed when a fluid including polymer is coated onto the hair, then hot-pressed and converted into a film with a nanostructured pattern that diffracts light into dispersed colored light. The temperatures used for hot pressing the solution-coated hair should be above the glass transition temperature (Tg) of the polymer. In an embodiment, the pressing temperature may be 20 to 30 degrees higher than the glass transition temperature of the polymer. The fluid and polymer therein should flow to conform to the nanostructured features of the nanostructured block of the hot pressing device. A suitable range for Tg of the polymer is a range from about 55 degrees Celsius to about 90 degrees Celsius. In an embodiment, the glass transition temperature of the polymer may not be above the temperature at which the hair may be noticeably damaged or burned.

Suitable polymers with a Tg from about 55 degrees Celsius to about 90 degrees Celsius include, but are not limited to, a poly-lactic acid, a polyvinyl alcohol, acrylic acids, acrylates, polyurethanes, copolymers thereof, and mixtures thereof.

In an embodiment, the material may be a polymer-containing solution. In an embodiment, the material may be a polymer-containing suspension. In an embodiment, the material may be a polymer-containing dispersion, such as a polymer-containing emulsion. In an embodiment, the material may be particles that are electrostatically attracted to the hair that melt under heat. The polymer-containing material may include a plasticizer. The polymer-containing material may include a surfactant. The polymer-containing material may include an emulsifier. These additional components may be optional components of the material so that it is suitable for coating the hair and for the subsequent heating that transforms the material into a film with a surface imprinted with a secondary nanostructured surface pattern capable of diffracting incident light into dispersed colors that are visible on the film-coated hair.

The film-coated hair after heat treatment may be thought of as a composite of the hair and the polymer-containing film that diffracts incident polychromatic light into dispersed colors. The polymer-containing material may include a liquid selected from the group consisting of water (providing an aqueous polymer-containing solution), alcohol (e.g. ethanol), and mixtures thereof.

No dyes may be required for the hair treatment process because the color results may be from diffraction of light and not from any dye. In an embodiment, the color results can be removed by wetting or shampooing the treated hair—suitable polymers may be polymers that are removable from the hair by wetting or shampooing. These include, but are not limited to, polymers such as polyvinyl alcohol and acrylates that are soluble and/or dispersible. In an embodiment, the color results may be removed by reheating the hair.

An embodiment device for treating hair may include a standard hair press with a thermal block comprising a primary nanostructured surface inserted into the hair press. After forming a composite of the hair with the polymer, the composite may be treated using the hair iron by hot pressing. The result of the treatment is a thin film composite of hair and polymer that diffracts light to produce color. In an embodiment, the composite may be treated with a pressing device that does not comprise a heating element.

An embodiment nano-patterned thermal block may be prepared using any known method and device for such as, but not limited to, focused ion beam (FIB), photonic lithography, e-beam lithography, tool machining, ruling engines, diamond turning devices, and any other method or device that can produce nanometer scale features.

FIG. 1 shows an embodiment sketch of hot pressing a sample of polymer-coated hair. It should be noted that the heating block 20 comprising the primary nanostructured surface 22 may be on both surfaces of the hot press 10 closest to the hair sample 24. The hot press 10 includes press jaws 12 and heating element 14 for heating the jaws 12. As FIG. 1 shows, adjacent each of jaws 12 is a platen 16. Adjacent one of platens 16 is a backing layer 18 such as a layer of a heat-resistant commercially available polymer such as but not limited to TEFLON. Adjacent the backing layer 18 is heating block 20 configured with a primary nanopatterned surface pattern 22 facing polymer-coated hair sample 24. The fluid-coated hair sample 24 is coated with the polymer-containing fluid that may optionally include one or more of a plasticizer, a surfactant, and an emulsifier. The fluid may be a dispersion containing a polymer, a plasticizer, a surfactant, and an emulsifier. Backing layer 26 (e.g. aluminum foil) adjacent sample 24 and platen 16, which is adjacent press jaw 12. FIG. 1 shows force being applied to jaws 12 in order to press the jaws 12 together, which squeezes together all elements in between the jaws (i.e. platens 16, backing layer 18, heating block 20 with surface 22, sample 24, and backing layer 26) while an electric current is sent to heating element 14, which heats the jaws 12 and makes the pressing a hot pressing. Enough current is sent to heat the device to a temperature suitable for forming a film imprinted with the nanopatterned surface 22 of heating block 20. As the sample of coated hair 24 is hot-pressed, a film forms with a surface imprinted with a nanopattern that complements the nanopatterned surface 22 facing the sample. The pressing may be continued for a suitable time, pressure, and temperature until the fluid that coats the hair conforms to the nanopatterned surface 22 so that a film having this nanopatterned surface may be formed that will diffract incident polychromatic light into dispersed colors of light. After the hot pressing, the pressing force is discontinued. The pressed sample may be removed from the hot press and allowed to cool.

Figure 2:
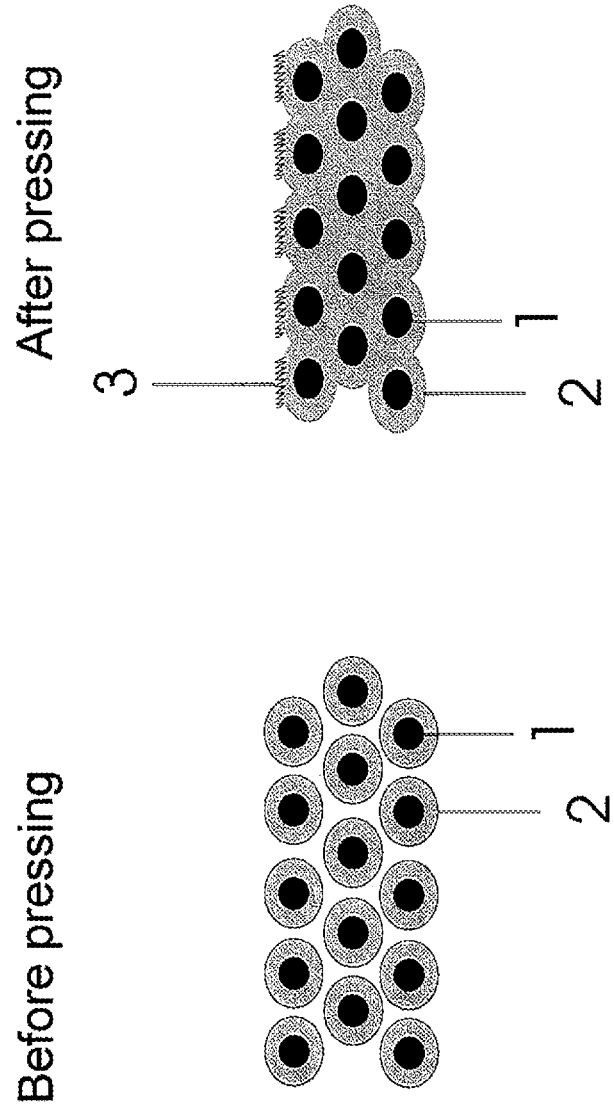
FIG. 2a shows a sketch of details of magnified fluid-coated hair prior to hot pressing.
FIG. 2b shows a sketch of the hair after hot pressing to form film with a nanostructured pattern that diffracts polychromatic light, producing dispersed colors.

FIG. 2a shows a "before pressing" sketch of details of magnified polymer-coated hair prior to hot pressing, and FIG. 2b shows an "after-pressing" sketch of the hair after hot pressing to form film with a secondary nanostructured surface pattern that diffracts light. The sketches are cross-sectional views. FIG. 2a shows individual strands from the hair sample coated with the polymer-containing material. The hair shafts 1 are each coated with the polymer-containing fluid 2. There is space in between individual strands of coated hair. A result of hot pressing may be a film that binds the individual hairs into a composite (FIG. 2b). As FIG. 2b shows, surface portions of the polymer film may be imprinted from the heating block surface 22 with a secondary nanostructured surface pattern 3 that diffracts incident polychromatic light into dispersed colors.

Figure 3:
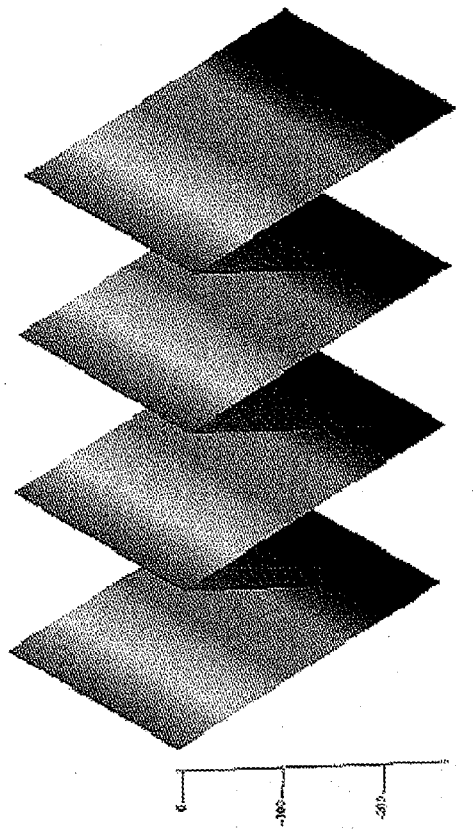
FIG. 3 shows a sketch of a sawtooth pattern that was formed in film coated hair that was shown to form dispersed colored light upon interaction with sunlight and theatrical light.

In an embodiment, a nanopatterned heating block 22 with a sawtooth pattern may be prepared and used to prepare a diffractive film from fluid-coated hair. A metal block with a sawtooth pattern may be prepared using a scribe machine to mill a sawtooth pattern into a metal blank. A soda-lime glass casting of the patterned metal may then be used as the heating block. The hair sample may be human hair that has been cleaned and dried. The hair sample may be hot pressed at a pressure of about 3-7 psi at a temperature above the glass transition temperature of the polymer. The result is a composite film including hair and polymer. The heating press comprising a surface comprising a primary nanostructured surface pattern may imprint a complementary sawtooth secondary nanostructured surface pattern into the film, shown in FIG. 3. This pressed sample may be demonstrated to form dispersed colors of light from polychromatic sunlight and theatrical light incident upon the sawtooth-patterned surface of the film.

A variety of other nano-patterned thermal blocks may be prepared using a focused ion beam (FIB). FIB pattern generator control files may be written for this purpose of forming nanopatterns suitable for light diffraction of incident polychromatic light.

Figure 4A:
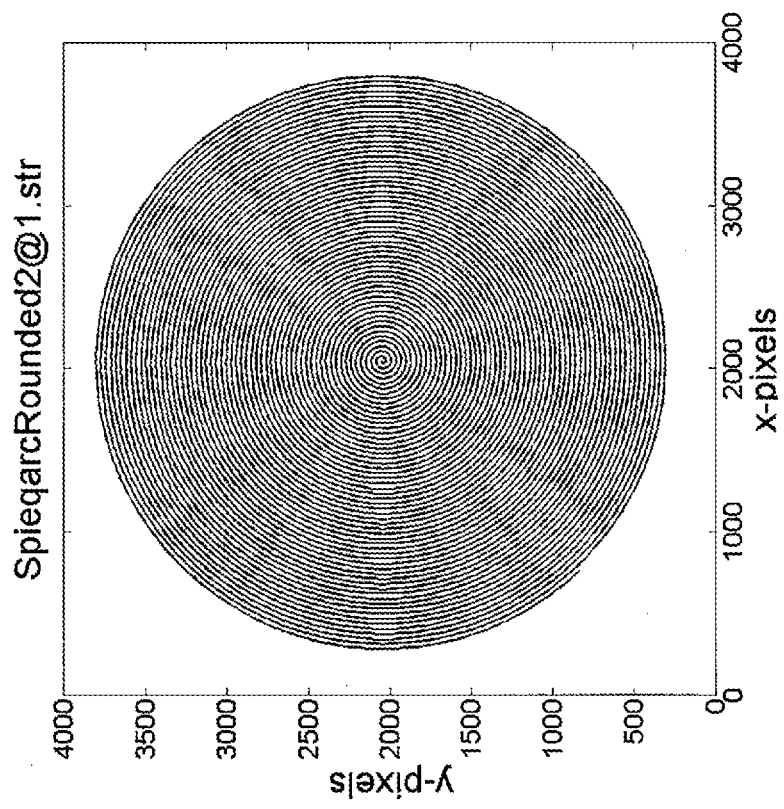
FIGS. 4a through 4e show nanopatterns including a spiral, parabola, and hyperbola that were milled into blanks to make embodiment heating blocks that were imprinted into polymer films that form dispersed colored light from incident polychromatic light such as sunlight and theatrical light.
Figure 4B:
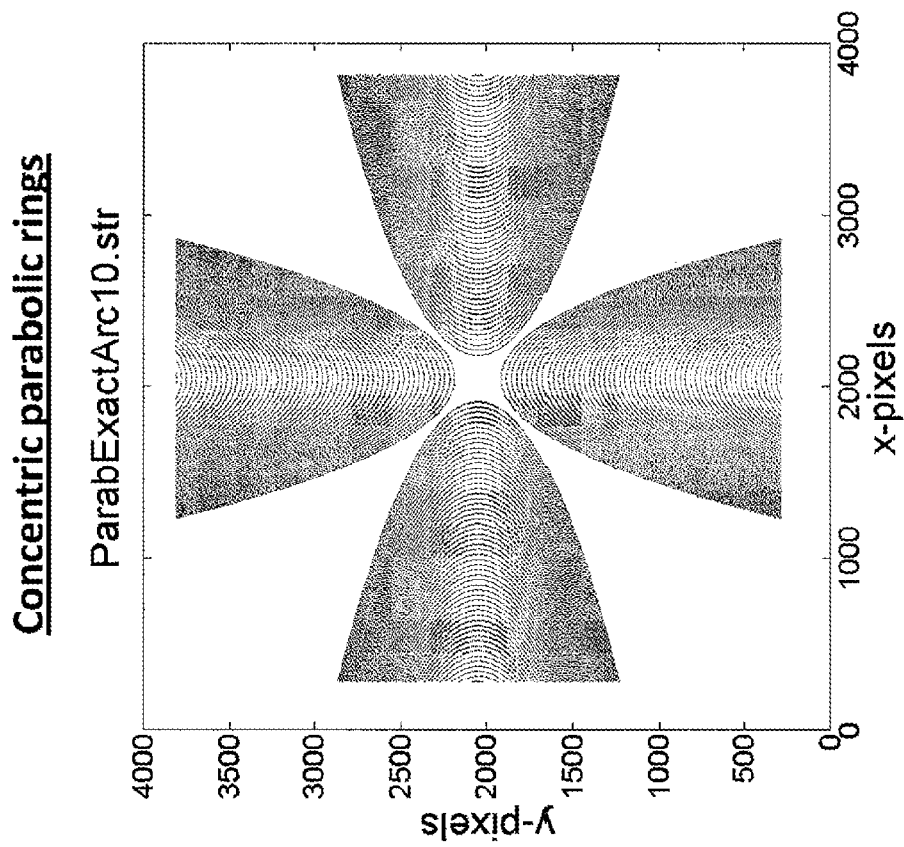
Figure 4C:
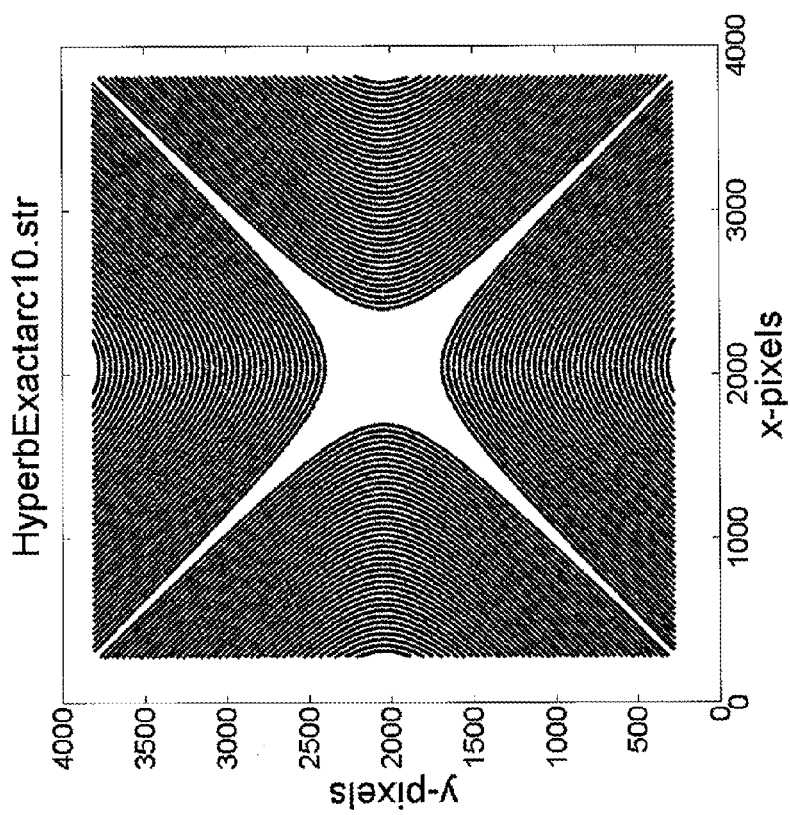
Figure 4D:
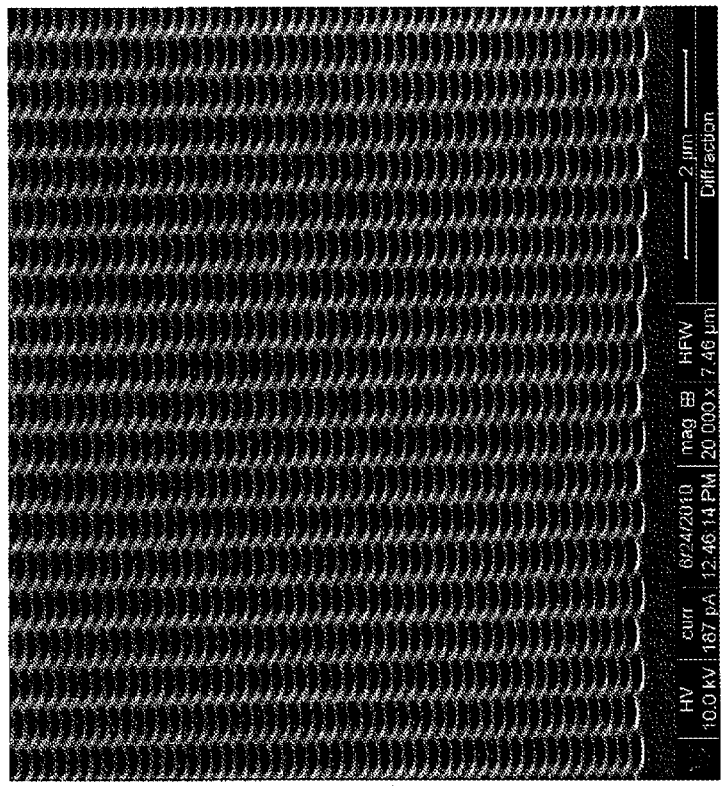
Figure 4E:
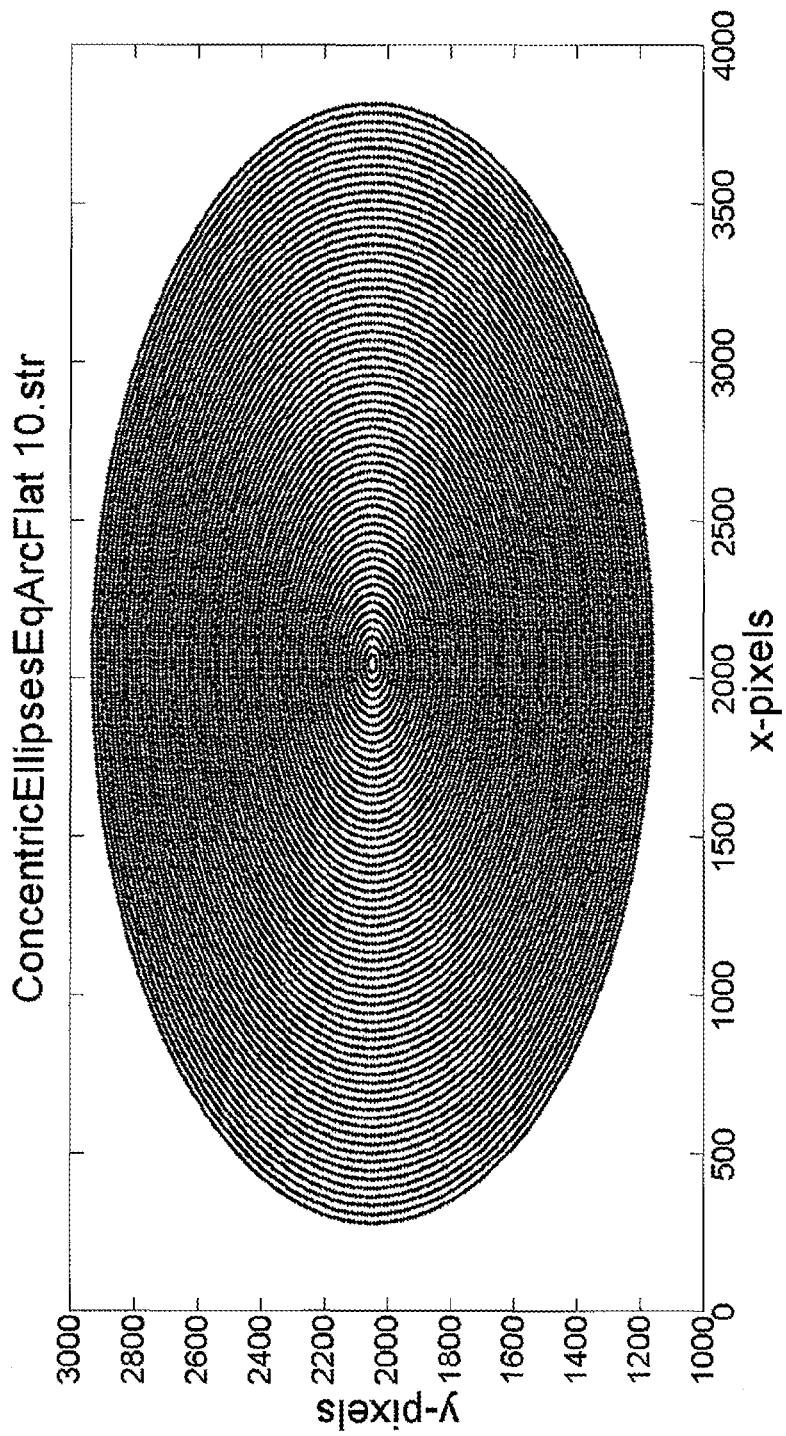

FIGS. 4a through 4e show several primary nanostructured surface patterns that may be prepared and may be imprinted into a surface of a polymer film that is not coated onto hair. FIG. 4a shows a spiral pattern with a circular envelope that may be milled to form a patterned block using the pattern generator control file SpieqarcRounded2@1.str. FIG. 4b shows a nanopattern of concentric parabolic rings that may be made using the pattern generator control file ParabExactArc10.str. FIG. 4c shows a nanopattern of concentric hyperbolic rings that may be made using the pattern generator control file HyperpbExactarc10.str. FIG. 4d shows a moth-eye pattern of rectangular pits with different pitch in vertical and horizontal directions that may be made using the pattern generator control file Smotheye2@30.str. FIG. 4e shows a spiral with an elliptical envelope that may be made using the pattern generator control file ConcentricEllipsesEqArcFlat10.str. Each of the nanopatterns may be milled into a metal blank to produce a nanopatterned heating block that may be imprinted into a polymer film that diffracts incident polychromatic light into dispersed colors. Hair provided with these types of films with these nanopatterns may diffract incident polychromatic light into dispersed colors.

A description of how FIB has been used for milling three-dimensional features on nanometer scale into media such as metal can be found in U.S. Pat. No. 5,773,116 and U.S. Pat. No. 5,721,687, both incorporated by reference. U.S. Pat. No. 6,583,933, incorporated by reference, also describes milling using a FIB to form aggregates of pits of low symmetry that produce directional diffraction gratings with blaze emphasizing a particular arbitrary spectral range.

A mastering process similar to that used for CDROM replication may be used to prepare nano-patterned heating blocks after first preparing a master block. To prepare the master block, a mill pattern may be written for a FIB milling device and applied to a master blank to convert the master blank into a master for the heating block. The master blank may be a metal blank made from a metal such as nickel, titanium, aluminum, tungsten, silicon, and the like. The master block may be used to prepare the primary nanostructured surface pattern on the heating block. Heating blocks may be made of, for example, soda lime glass.

It is envisioned that a commercially available pressing device such as a heating hair iron may be modified according to an embodiment of this invention by replacing one or more heating blocks in a commercially available hair iron with one or more heating blocks suitably configured with a surface comprising a primary nanostructured surface pattern such as the aforementioned sawtooth nanopattern or some other nanopattern such as a nanopattern shown in FIG. 4. A nano-patterned heating block prepared by FIB milling, or by some other process for creating suitable nanopatterns, may be used to modify one or more heating blocks of the commercially available heating device. Alternatively, a blank heating block adapted to fit into the commercially available heating iron may be milled with a primary nanostructured surface pattern suitable for heating solution-coated hair and imprinting a complimentary secondary nanostructured surface pattern into the resulting film. It is envisioned that a commercially available heating iron, may be modified to produce a pressing device that may be used to treat fluid-coated hair according to the aforementioned process for providing hair with a film imprinted with a secondary nanostructured surface pattern that would diffract incident polychromatic light into dispersed colors. This way, a person could treat their own hair or another person's hair according to an embodiment of this invention and provide their own hair or another person's hair with a nanopattern-imprinted polymer-containing film that diffracts polychromatic light such as sunlight or theatrical light into dispersed colored light.

The method of the invention may be demonstrated using human hair and commercially-available polymer-containing fluids known by the commercial name KOLLICOAT MAE 100P. These fluids are dispersions that are reported to include a 1:1 copolymer of methacrylic acid and ethyl acrylate. They have been reported to also include sodium laurate and polysorbate 80, which are a surfactant and emulsifier derived from polyethoxylated sorbitan and oleic acid. In an embodiment, samples of human hair may be mixed with the KOLLICOAT MAE 100P. In one embodiment, an 18% by weight dispersion of KOLLICOAT MAE 100P in water may be used to prepare a hair-polymer film composite having a thickness of 13 micrometers. In another embodiment, a 4.2% by weight dispersion of KOLLICOAT MAE 100P in ethanol with 10% triethyl citrate plasticizer may be used to prepare a hair-polymer film composite having a thickness of 3-4 micrometers. Each of the films after hot pressing with a nanopatterned heating block may diffract polychromatic light into dispersed colors.

It should be understood that the invention is not to be limited to using any particular polymer-containing material with any particular added components of plasticizers, surfactants, emulsifiers, and the like, and that any polymer-containing material suitable for forming a film on the hair after hot pressing or pressing to conform to a suitable primary nanostructured surface pattern on a pressing device is within the scope of this invention.

The invention is not limited to any particular nanopattern. Patterns may be produced according to fashion whim. Suitable nanopatterns are any that are capable of diffracting polychromatic light into dispersed colors of light.

An embodiment of the treatment may provide color images that appear momentarily as the hair moves on the head. Movement of the head results in changing the relationship between the film-coated hair and someone looking at the hair. A person looking at the hair detects the dispersed colors, which appear when the angle of reflection of the incident light permits the viewer to observe the dispersion of the colors.

This hair treatment process may provide a means for arbitrary directional control of color reflected from illuminated hair, and for embedding local iridescent color regions into hair using suitable nanopatterns that diffract light into dispersed colors.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair treatment process for providing dispersed colors by light diffraction comprising:
   a. coating the hair with a material comprising a polymer;
   b. pressing a section of the hair with a pressing device comprising a heating block comprising one or more surfaces, wherein the one or more surfaces each comprise a primary nanostructured surface pattern; and
   c. forming a secondary nanostructured surface pattern on the section of the hair that is complementary to the primary nanostructured surface pattern on the one or more surfaces of the pressing device;
   wherein the secondary nanostructured surface pattern diffracts light into dispersed colors that are visible on the section of the hair; and
   wherein the section of the hair is pressed with the pressing device for from about 1 to 55 seconds.

2. The hair treatment process of claim 1, wherein the material is aqueous.

3. The hair treatment process of claim 1, wherein the material comprises a plasticizer.

4. The hair treatment process of claim 1, wherein the material comprises a surfactant.

5. The hair treatment process of claim 1, wherein the polymer has a glass transition temperature of from about 55° C. to about 90° C.

6. The hair treatment process of claim 1, wherein the polymer is selected from the group consisting of poly-lactic acid polymers, acrylate polymers, polyvinyl alcohol polymers, polyurethanes, copolymers thereof, and combinations thereof.

7. The hair treatment process of claim 1, wherein the section of the hair is pressed with the pressing device at a pressure of from about 3 psi to about 7 psi.

8. The hair treatment process of claim 1, wherein the section of the hair is pressed with the pressing device at a temperature above the glass transition temperature of the polymer.

9. The hair treatment process of claim 1, wherein the primary nanostructured surface pattern is selected from the group consisting of sawtooth patterns, spiral patterns, ring patterns, Archimedean patterns, ellipsoidal patterns, patterns comprising hyperbolic rings, patterns comprising parabolic rings, and combinations thereof.

10. A hair treatment process for providing dispersed colors by light diffraction comprising:
   a. coating the hair with a material comprising a polymer;
   b. pressing a section of the hair with a pressing device comprising a heating block comprising two or more surfaces, wherein the two or more surfaces each comprise a primary nanostructured surface pattern; and
   c. forming a secondary nanostructured surface pattern on the section of the hair that is complementary to the primary nanostructured surface patterns on the two or more surfaces of the pressing device;
   wherein the secondary nanostructured surface pattern diffracts light into dispersed colors that are visible on the section of the hair.

11. The hair treatment process of claim 10, wherein the section of the hair is pressed with the pressing device for from about 1 to 55 seconds.

12. The hair treatment process of claim 10, wherein the material is aqueous.

13. The hair treatment process of claim 10, wherein the material comprises a plasticizer.

14. The hair treatment process of claim 10, wherein the material comprises a surfactant.

15. The hair treatment process of claim 10, wherein the polymer has a glass transition temperature of from about 55° C. to about 90° C.

16. The hair treatment process of claim 10, wherein the polymer is selected from the group consisting of poly-lactic acid polymers, acrylate polymers, polyvinyl alcohol polymers, polyurethanes, copolymers thereof, and combinations thereof.

17. The hair treatment process of claim 10, wherein the section of the hair is pressed with the pressing device at a pressure of from about 3 psi to about 7 psi.

18. The hair treatment process of claim 10, wherein the section of the hair is pressed with the pressing device at a temperature above the glass transition temperature of the polymer.

19. The hair treatment process of claim 10, wherein the primary nanostructured surface pattern is selected from the group consisting of sawtooth patterns, spiral patterns, ring patterns, Archimedean patterns, ellipsoidal patterns, patterns comprising hyperbolic rings, patterns comprising parabolic rings, and combinations thereof.

20. A hair treatment process for providing dispersed colors by light diffraction comprising:
   a. coating the hair with a material comprising a polymer;
   b. pressing the hair with a pressing device comprising a heating block comprising one or more surfaces, wherein the one or more surfaces each comprise a primary nanostructured surface pattern; and
   c. forming a secondary nanostructured surface pattern on the hair that is complementary to the primary nanostructured surface pattern on the one or more surfaces of the pressing device;
   wherein the secondary nanostructured surface pattern diffracts light into dispersed colors that are visible on the hair; and
   wherein the press does not comprise a heating element.

* * * * *